United States Patent
Cohen-Solal et al.

(10) Patent No.: US 10,614,335 B2
(45) Date of Patent: Apr. 7, 2020

(54) MATCHING OF FINDINGS BETWEEN IMAGING DATA SETS

(71) Applicant: KONINKLIJKE PHILIPS N.V., Eindhoven (NL)

(72) Inventors: Eric Cohen-Solal, Ossining, NY (US); Gabriel Ryan Mankovich, Yorktown Heights, NY (US); Yuechen Qian, Briarcliff Manor, NY (US); Thusitha Dananjaya De Silva Mabotuwana, Yonkers, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 546 days.

(21) Appl. No.: 14/906,608

(22) PCT Filed: Jul. 8, 2014

(86) PCT No.: PCT/IB2014/062936
§ 371 (c)(1),
(2) Date: Jan. 21, 2016

(87) PCT Pub. No.: WO2015/015341
PCT Pub. Date: Feb. 5, 2015

(65) Prior Publication Data
US 2016/0162745 A1 Jun. 9, 2016

Related U.S. Application Data

(60) Provisional application No. 61/859,884, filed on Jul. 30, 2013.

(51) Int. Cl.
*A61B 3/113* (2006.01)
*A61B 5/00* (2006.01)
(Continued)

(52) U.S. Cl.
CPC ............ *G06K 9/2081* (2013.01); *A61B 3/113* (2013.01); *A61B 5/7425* (2013.01); *G06F 3/013* (2013.01);
(Continued)

(58) Field of Classification Search
None
See application file for complete search history.

(56) References Cited

U.S. PATENT DOCUMENTS 6,381,339 B1    4/2002  Brown et al.
7,573,439 B2 *  8/2009  Lau ........................ G06F 3/013
                                                        345/7

(Continued)

FOREIGN PATENT DOCUMENTS

CN    102883660 A    1/2013
JP    H0370381 A     3/1991
JP    2007029248 A   2/2007

OTHER PUBLICATIONS

Anderson et al., "A preliminary study to understand tacit knowledge and visual routines of medical experts through gaze tracking," AMIA Annu Symp Proc. 2010; 2010: 21-25.*

(Continued)

*Primary Examiner* — Soo Shin

(57) ABSTRACT

A method includes detecting a focus of attention of an observer of an anatomical image of a set of images, determining a location of the anatomical image includes tissue with a finding of interest based on the detected focus of attention, identifying an anatomical image, from an earlier acquired imaging data set, with a same portion of tissue as the displayed image, visually displaying graphical indicia, concurrently with the displayed image, that identifies the earlier acquired image.

11 Claims, 4 Drawing Sheets

(51) Int. Cl.
*G06F 19/00* (2018.01)
*G06F 3/01* (2006.01)
*G06K 9/20* (2006.01)
*G06K 9/62* (2006.01)
*G06T 7/00* (2017.01)

(52) U.S. Cl.
CPC ......... *G06F 19/321* (2013.01); *G06K 9/6202* (2013.01); *G06T 7/0014* (2013.01); *G06T 2207/20101* (2013.01); *G06T 2207/30004* (2013.01)

(56) References Cited

U.S. PATENT DOCUMENTS

| | | |
|---|---|---|
| 7,593,602 B2 | 9/2009 | Stentiford |
| 7,747,050 B2 | 6/2010 | Lau et al. |
| 8,020,993 B1* | 9/2011 | Fram ............ G06F 3/013 351/200 |
| 2006/0112334 A1* | 5/2006 | Endrikhovski ...... G06F 3/013 715/700 |
| 2009/0132279 A1* | 5/2009 | Yeluri ............ G06F 17/30277 705/3 |
| 2009/0146775 A1 | 6/2009 | Bonnaud et al. |
| 2009/0153472 A1 | 6/2009 | Bloem et al. |
| 2011/0270123 A1* | 11/2011 | Reiner ............ A61B 6/463 600/558 |
| 2012/0014559 A1* | 1/2012 | Suehling ............ G06K 9/6207 382/103 |
| 2013/0024208 A1 | 1/2013 | Vining |
| 2015/0169052 A1* | 6/2015 | Kramer ............ G06F 3/013 345/156 |

OTHER PUBLICATIONS

Gegenfurtner et al., "Expertise differences in the comprehension of visualizations: a meta-analysis of eye-tracking research in professional domains," Educ Psychol Rev, Dec. 2011, 23(4): 523-552.*
Li et al., "Learning image-derived eye movement patterns to characterize perceptual expertise," Proceedings of the Annual Meeting of the Cognitive Science Society, vol. 34, 2012.*
Holmqvist, K. et al., "Eye Tracking: A comprehensive guide to methods and measures", Oxford University Press, 2010.

* cited by examiner

MATCHING OF FINDINGS BETWEEN IMAGING DATA SETS

CROSS-REFERENCE TO PRIOR APPLICATIONS

This application is the U.S. National Phase application under 35 U.S.C. § 371 of International Application No. PCT/IB2014/062936, filed on Jul. 8, 2014, which claims the benefit of U.S. Provisional Application No. 61/859,884, filed on Jul. 30, 2013. These applications are hereby incorporated by reference herein.

The following generally relates to imaging and more particularly to matching of findings between imaging data sets.

Radiologists routinely read and interpret images. This includes images of follow-up cases where progression of treated lesions (e.g. chemotherapy) or results of an intervention (e.g. surgery) are monitored over time. In such cases, the radiologist reports on noticeable and significant changes corresponding to specific clinical questions (shrinking tumor, correctly-healing tissue after surgery, etc.).

Patient follow-up may include consecutive studies performed with the same imaging protocols (i.e. same modality, same scanned body part and scanner parameters). These studies can contain hundreds of slices to be looked at. The original study will often contain key images that have been marked as the radiologist reviews the case. In a follow-up study, the radiologist will report on the previously marked findings (annotated within key images).

For this, the radiologist scrolls through images in a current study to determine the relevant images that closely correspond to findings identified on prior studies. This task is performed by visually comparing the current study images with prior study images, going back and forth between the two image sets. Unfortunately, this can be a monotonous task, where the radiologist locates each finding in the new study and compares each of them to the right and corresponding finding in the prior study.

Aspects described herein address the above-referenced problems and others.

The following describes an approach to match findings between a current image data set and a prior study and, optionally, provide a notification when a match is found. The user can then decide to follow-up on the suggestion and display the matching image slice and location of the relevant finding in the prior study. In one instance, this avoids having to have the clinician go through all the prior image slices for a given series in search of a corresponding finding, resulting in a much quicker visual comparison, faster finding annotation and report editing. This approach can also identify when a new finding in a current image data set has not been annotated in the previous image data set, when a finding in the previous image data set may have been missed in the current image data set, and/or reduce the scan extent (and hence dose) in a follow-up imaging procedure.

In one aspect, a method includes detecting a focus of attention of an observer of an anatomical image of a set of images, determining a location of the anatomical image includes tissue with a finding of interest based on the detected focus of attention, identifying an anatomical image, from an earlier acquired imaging data set, with a same portion of tissue as the displayed image, visually displaying graphical indicia, concurrently with the displayed image, that identifies the earlier acquired image.

In another aspect, a system includes a sensor that senses a focus of attention of an observer of an anatomical image, of a set of images, displayed on a monitor, a mapper that maps the focus of attention to the image based on a display geometry of the monitor, a metric determiner that determine a metric based on the map, logic that compares the metric with a predetermined metric and determines a location of the anatomical image includes tissue with a finding of interest in response to the metric satisfying the predetermined metric, an image selector that identifies an anatomical image, from an earlier acquired imaging data set, with a same tissue as the displayed image, and a display monitor that displays graphical indicia that identifies the earlier acquired image.

In another aspect, a computer readable storage medium is encoded with computer readable instructions, which, when executed by a processer, causes the processor to: detect a focus of attention of an observer of an anatomical image, of a set of images, displayed on a monitor, determine a location of the anatomical image includes tissue with a finding of interest based on the focus of attention, identify an anatomical image, from an earlier acquired imaging data set, with a same tissue as the displayed image, and visually displaying graphical indicia, concurrently with the image, that identifies the earlier acquired image.

The invention may take form in various components and arrangements of components, and in various steps and arrangements of steps. The drawings are only for purposes of illustrating the preferred embodiments and are not to be construed as limiting the invention.

FIG. 1 schematically illustrates a computing system in connection with an imaging system(s) and a data repository.

Figure 1:
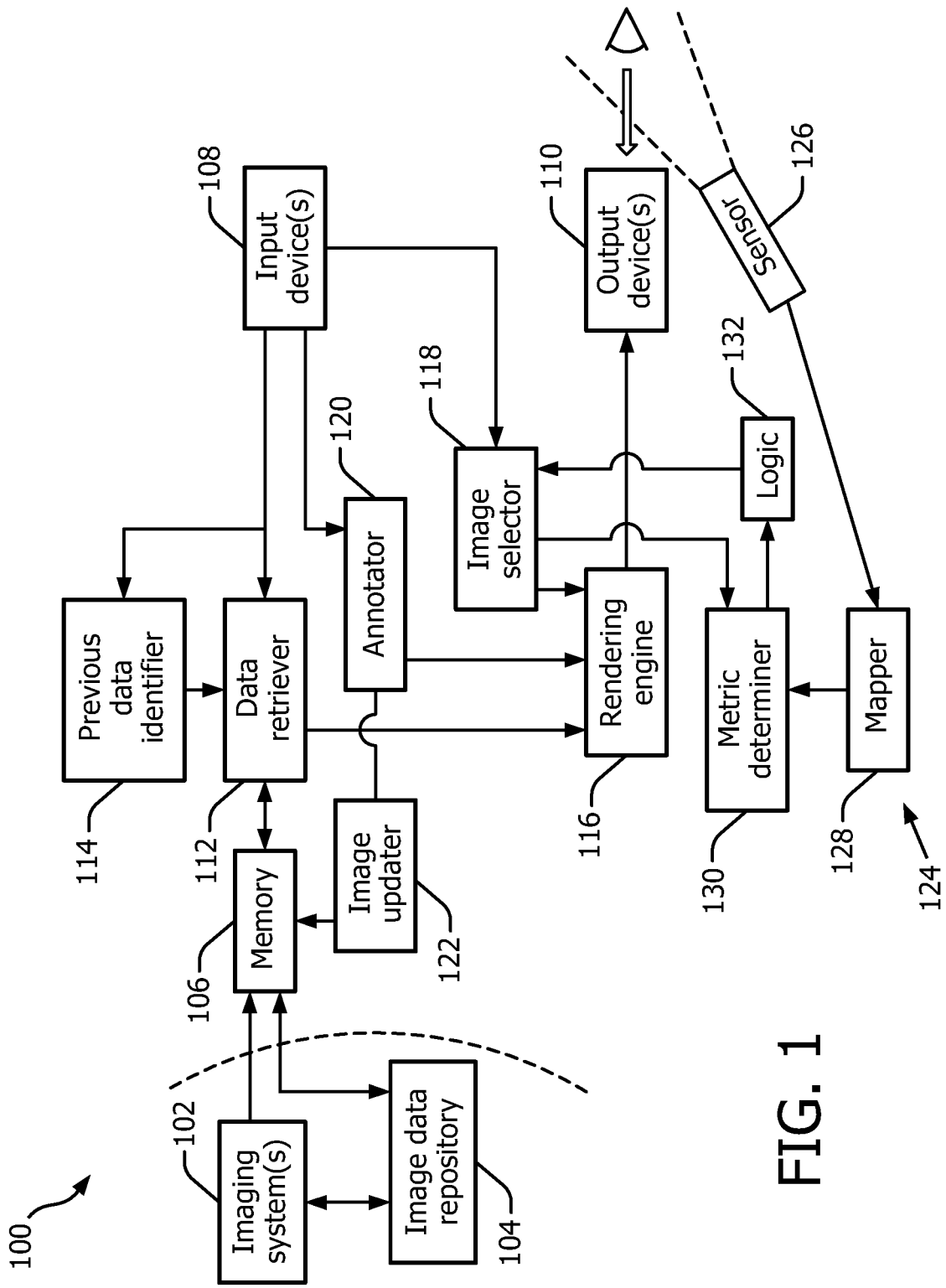

FIG. 1 schematically illustrates a computer system 100 in connection with an imaging system(s) 102 and/or a data repository 104. Imaging data may be stored by and/or transferred between the computer system 100, the imaging system(s) 102, and/or the data repository 104 in standard formats such as Digital Imaging and Communications in Medicine (DICOM), Health Level 7 (HL7), and/or other standard formats, and/or non-standard, proprietary, and/or other format.

The imaging system(s) 102 includes for example one or more of a computed tomography (CT), a magnetic resonance imaging (MM), a positron emission tomography (PET), single photon emission computed tomography (SPECT), X-ray, and/or other imaging system. The data repository 104 includes for example one or more of a picture archiving and communication system (PACS), a radiology information system (RIS), a hospital information system (HIS), and/or other data repository.

The computer system 100 includes one or more microprocessors and computer readable storage medium (memory) 106 (i.e., physical memory and other non-transitory storage medium). The computer system 100 further includes an input device(s) 108 such as a keyboard, a mouse, a microphone, a touchscreen, etc.) and an output device(s) 110 such as a monitor, a filmer, a printer, etc.

The computer readable storage medium 106 is encoded with computer readable instructions, which, when executed by the one or more microprocessors cause the system 100 to carry out the various functions described herein. The one or more microprocessors can additionally or alternatively execute instructions carried by a carrier wave, a signal and other transitory storage medium.

The computer system 100 further includes a data retriever 112 that receives as an input, via the input device(s) 108, a signal identifying an imaging data set to retrieve for a patient. For this, the computer system 100 may first visually present in a graphical user interface (GUI) or the like a list of stored patient studies, from which a user can select an imaging data set to load.

The user selects one of the imaging data sets via the input device(s) 108. In the illustrated example, the data retriever 112 retrieves the imaging data set from the memory 106, the imaging system(s) 102, and/or the image data repository 104. The selected imaging data set may be an initial imaging data set of the patient to be read or a follow-up imaging data set of the patient for reading and comparison with a previously generated data set of the patient.

Where the signal identifies a follow-up imaging data set, a previous data identifier 114 is used to identify a previously generated and stored imaging data set corresponding to the follow-up imaging data set. The previously generated and stored imaging data set is identified as related to a follow-up imaging data set for example based on imaging protocol, scanned anatomy of interest, imaging modality, and/or other data, and/or by the most recent (chronologically) scan of the patient.

The previous data identifier 114 can instead be employed during observation of images of the follow up imaging data set. In this instance, a previously generated image from a previously generated image data set is identified by computing a normalized weighted score between the currently observed image and images of the data sets. For example, if an image is generated with data from a same modality, a binary count of 1 is added to the score. The same counting is done for anatomy, series, image slice number, etc.

As a result, each finding has a real-time score. If a highest score passes a certain threshold, the images are considered a match. In a variation, a time constraint may be used to limit the considered prior studies, either by filtering only the most recent ones or by introducing a time-decay function as part of the normalized weighted score mentioned earlier. Other approaches are also contemplated herein.

A rendering engine 116 visually presents the retrieved imaging data via a monitor of the output device(s) 110. Where the signal identifies a follow-up imaging data set, both the follow-up image and the previously generated image are displayed. The two imaging data sets can be displayed using multiple monitors, one data set per monitor, or a single monitor, e.g., using split screen, toggle back and forth, and/or other approach.

An image selector 118 allows an operator, via the input device(s) 108, to scroll, jump, and/or otherwise navigate through and select an image (slice) for the rendering engine 116 to visually present via the monitor of the output device(s) 110. The image selector 118 maintains, in real-time, the displayed image slice number, the series in an imaging examination data, etc.

An annotator 120, receives as an input, via the input device(s) 108, a signal identifying an annotation to superimpose or overlay over a displayed image. The annotation is conveyed to the rendering engine 116 to visually present via the monitor of the output device(s) 110. The annotator 120 also allows for propagating an annotation of one image to another image.

An image updater 122 updates the corresponding image in the memory 106 to include the annotation and/or a field of a file in which the image is part of to include the annotation. The annotated imaging data set is for example stored in DICOM format in which the header includes: a modality, an anatomical region, an imaging protocol, a key image, a finding, an annotation, a location, a slice number, a series identifier, a finding characteristic (e.g., shape, margin, size, etc.), lesion delineation (e.g., provided by user or any automatic or semi-automatic segmentation method), and/or other information.

An eye tracker 124 detects or tracks a focus of attention of an observer of an anatomical image of a set of images. Generally, the eye tracker 124 can employ any approach that can identify focus-of-attention regions. Examples of suitable approaches are discussed in "Eye Tracking: A comprehensive guide to methods and measures," by Kenneth Holmqvist, Marcus Nyström, Richard Andersson, Richard Dewhurst, Halszka Jarodzka, Joost van de Weijer, Oxford University Press, 2011. These approaches include line of sight, eye movement, pattern of eye movement, dwelling, etc. Other approaches are also contemplated herein.

By way of non-limiting example, in one non-limiting approach, the eye tracker 124 measures a point of gaze and/or motion of an eye(s) of an observer observing a follow up image displayed via the output device(s) 110 relative a geometry of a display area of the output device(s) 110 and generates a signal indicative thereof. The illustrated eye tracker 124 includes a sensor 126 such as a video camera or the like. Other sensors are also contemplated herein. The sensor 126 is for example mounted on a device such as a table, a stand, the computing system 100, etc., a head set worn by the observer, and/or otherwise.

The illustrated sensor 126 focuses on one or both eyes of the observer and records their movement as the observer observes an image displayed via the output device(s) 110. In one non-limiting instance, the sensor 126 focuses on the center of the pupil and senses visible and/or infrared/near-infrared non-collimated light to create corneal reflections. The vector between the pupil center and the corneal reflections can be used to compute a point of regard on surface or the gaze direction.

The eye tracker 124 further includes a mapper 128 that processes the signal from the sensor 126 and maps the gaze and/or motion of the eye(s) to a coordinate system (the x,y coordinates) of the monitor of the output device(s) 110. The mapper 128 generates a signal indicative of the mapping. The mapping, in one instance, provides a time based mapping of the line of sight with respect to the plane of the monitor for each observed image.

A metric determiner 130 receives the output of the mapper 128 and/or the output of the image selector 118 and generates one or more metrics based thereon. For example, in one instance, the metric determiner 130 processes the output of the mapper 128 and generates a metric that indicates a total amount of time the observer spent observing each location within each image for each observed image. In another instance, the metric determiner 130 processes the output of the image selector 118 and generates a metric that indicates a sequential order in which the images are observed.

Logic 132 evaluates the metrics. In one instance, this includes comparing the metrics against predetermined threshold and/or a pattern of observation. For example, the metric indicating a total amount of time the observer spent observing each location within the image can be compared with the time threshold, and the metric indicating the sequential order in which the images are observed can be compared with the pattern of observation.

In one instance, satisfying the threshold indicates that the location of the displayed image being observed includes a feature of interest to the observer. That is, if the observer spends at least the threshold amount of time observing a particular location in an image and/or scrolls back and forth several times through a sub-set of images, the logic 132 determines that the location in the image or a 3D location in the series of images includes a finding of interest to the observer.

In response to a metric satisfying a threshold in connection with observing an image of a follow-up imaging data set, the logic 132 invokes the image selector 118 to concurrently display the corresponding image from the previously generated and stored imaging data set. In one instance, the particular image can be identified by computing a distance to a prior finding localized by an annotation, where a shortest distance below a given threshold is identified as the corresponding image.

In a variation, the logic 132 may register (e.g., model-based or segmentation-based) images in order to have the same anatomical regions geometrically corresponding between them (e.g., organ level, slice number, location within a slice). This may improve the precision of the matching. Rigid and/or elastic registration algorithms can be used. Where the imaging data sets correspond to different modalities (e.g., CT and MR), a registration or fusion of the two types of images can be performed.

In another variation, the logic 132 may employ segmentation using the eye tracking location as a seed to initiate the segmentation of a finding (e.g., mass, tumor, cyst, etc.). This may provide a more accurate location of a prior finding for matching, not based on the annotation provided by the user but based on the object itself. In addition, this provides an ability to compute a shape, a margin and/or any other feature(s) to further compute the matching score and avoid mismatch (i.e. appearance-based matching).

Conversely, if the threshold is not satisfied, the logic 132 determines that a location in an image does not include a feature of interest to the observer and does invoke display of any image.

By automatically displaying the corresponding image, the observer need not have to scroll through the previously generated imaging data set to find this image, saving time. The logic 132 can display visual feedback or indicia such as an icon, text, a graphic, etc. over the display of the follow-up image, apprising the observer that a match was found and is displayed on the other monitor. The observer, via the input device(s) 108 and the annotator 120, can annotate the follow up image and/or the previously generated image.

In a variation, the indicia is displayed without displaying the previously generated image. In this instance, the previously generated image and/or the annotation is displayed upon clicking on the indicia and/or otherwise invoking display. In this case, the observer can confirm that the identified previously generated image indeed does correspond to the follow up image being observed prior to displaying the previously generated image. The observer, via the input device (s) 108, can reject or accept the image mapping.

By way of non-limiting example, the logic 132 can display an icon at the level of the observer's gaze and at the side of the screen to visually notify the observer. Alternatively, an arrow can appear on the image at the level of the match and gaze location along with an audio signal. If the observer decides to consider the match, the observer can hover a mouse over and/or click on the icon and the corresponding finding in a prior study appears on the other monitor to evaluate and confirm the match.

In the case where the observer confirms a correct match, the observer can seamlessly edit the image annotation and associated text description starting with the prior finding description. The text from the prior study can be propagated and displayed in a small window on the side of the current finding. When done and submitted, finding details will be added to the final report. Image annotation from the prior finding can also be positioned at the gaze location in the current image for final edition.

The following provides a non-limiting use case scenario. In this example, the system 100 is a PACS system. However, in other examples, the system 100 can be another computer system.

An initial imaging exam is ordered by a referring or a specialty physician (e.g. an oncologist, a cardiologist, etc.) to reach or confirm a diagnosis for a patient presenting with a new medical condition. For example, the patient may consult his/her referring physician with symptoms of intermittent abdominal pain, and the physician provides an order for a CT abdomen-pelvis imaging exam.

The system 100 (and/or other system) is utilized to view image slices of the resulting volumetric imaging data set. This includes utilizing the annotator 120 to annotate features of interest represented in one or more of the images and generating a radiology report for this new medical condition. The annotated imaging data set is saved to memory 106, in the data repository 104, and/or other storage. The particular storage may include some or all of the studies for each patient.

When the patient returns for a follow-up exam or for a monitoring purpose during or after treatment, the system 100 reduces the navigation effort to go over the stack of prior images by suggesting potential matches between a present finding currently observed by the radiologist and prior ones from past studies.

Optionally, the system 100 can be used to identify overlooked findings in a prior study: For example, if the observer visually detects a new finding in the current study which was not seen and reported before (no suggested match by the invention), the logic 132 invokes the image selector 118 to display the corresponding region from the most recent prior study (slice number and series) where the overlooked finding might be located.

For this, the observer's gaze provides the location of the newly detected finding in an image from the current study. The observer can, for instance through speech recognition or other approaches, ask the system 100 to look for an equivalent location in a prior study. The corresponding slice is displayed for comparison. The observer might discover the overlooked finding, possibly smaller and less detectable.

For ignored findings in the current study. If the radiologist visually fails to examine areas in the current study that correspond to findings in prior study, the system can notify and visualize those ignored prior findings in their corresponding areas of the current study. This can be done dynamically as the radiologist already past the findings scrolling down the stack of images or later when the reading phase is completed to notify the radiologist of one or more overlooked regions.

The foregoing may also be used to restrict acquisition of a subsequent scan, which may reduce the x-ray dose the patient receives, relative to not restricting the subsequent scan. For this, the logic 132 determines the corresponding regions between the prior findings location, associated organs and sub-regions and suggests an imaging extent to restrict the acquisition to only the regions useful for comparison.

Figure 2:
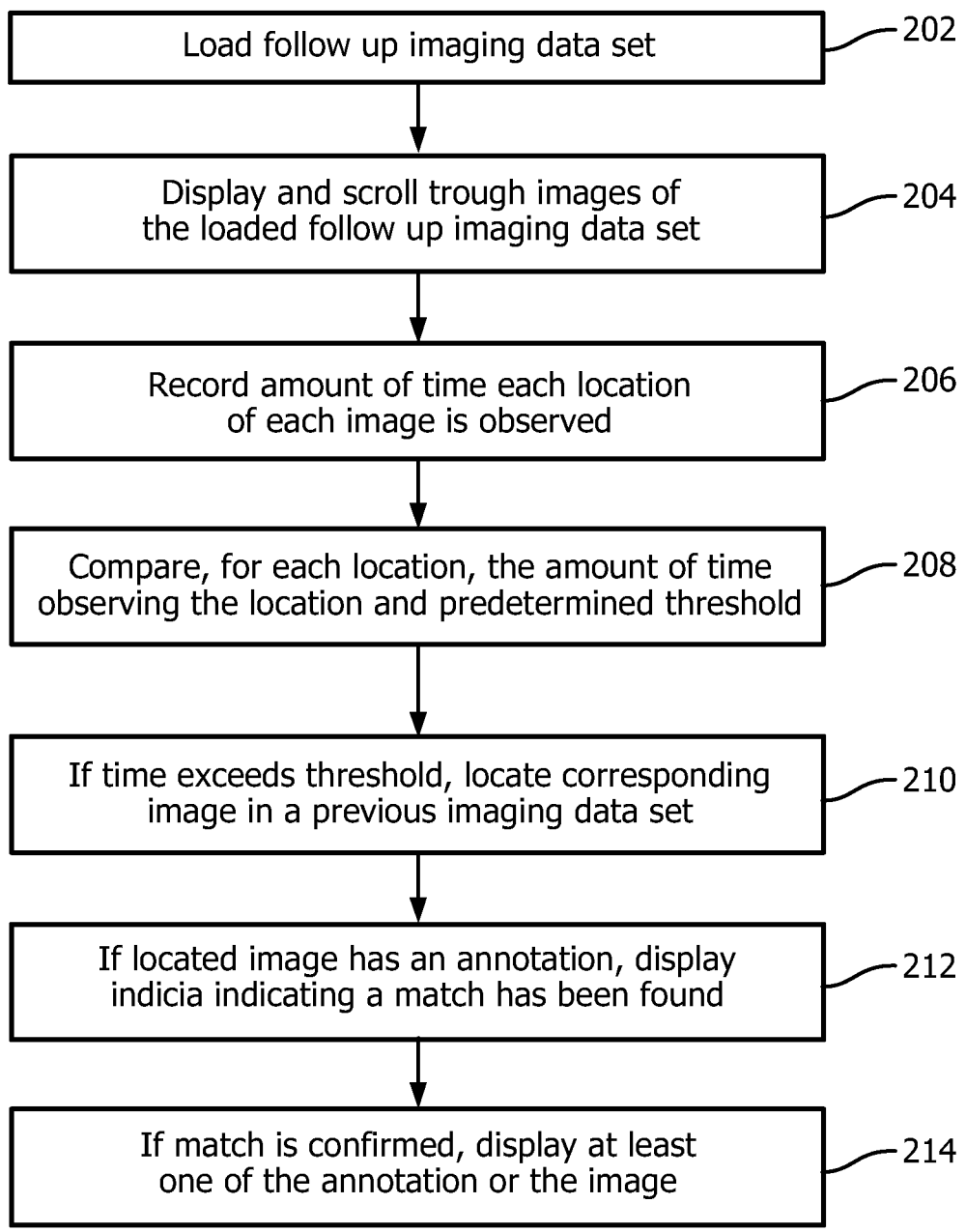
FIG. 2 illustrates a method for identifying and displaying a previous image with an annotation in a previously acquired data set corresponding to a current image with a finding of interest in a current data set.
Figure 3:
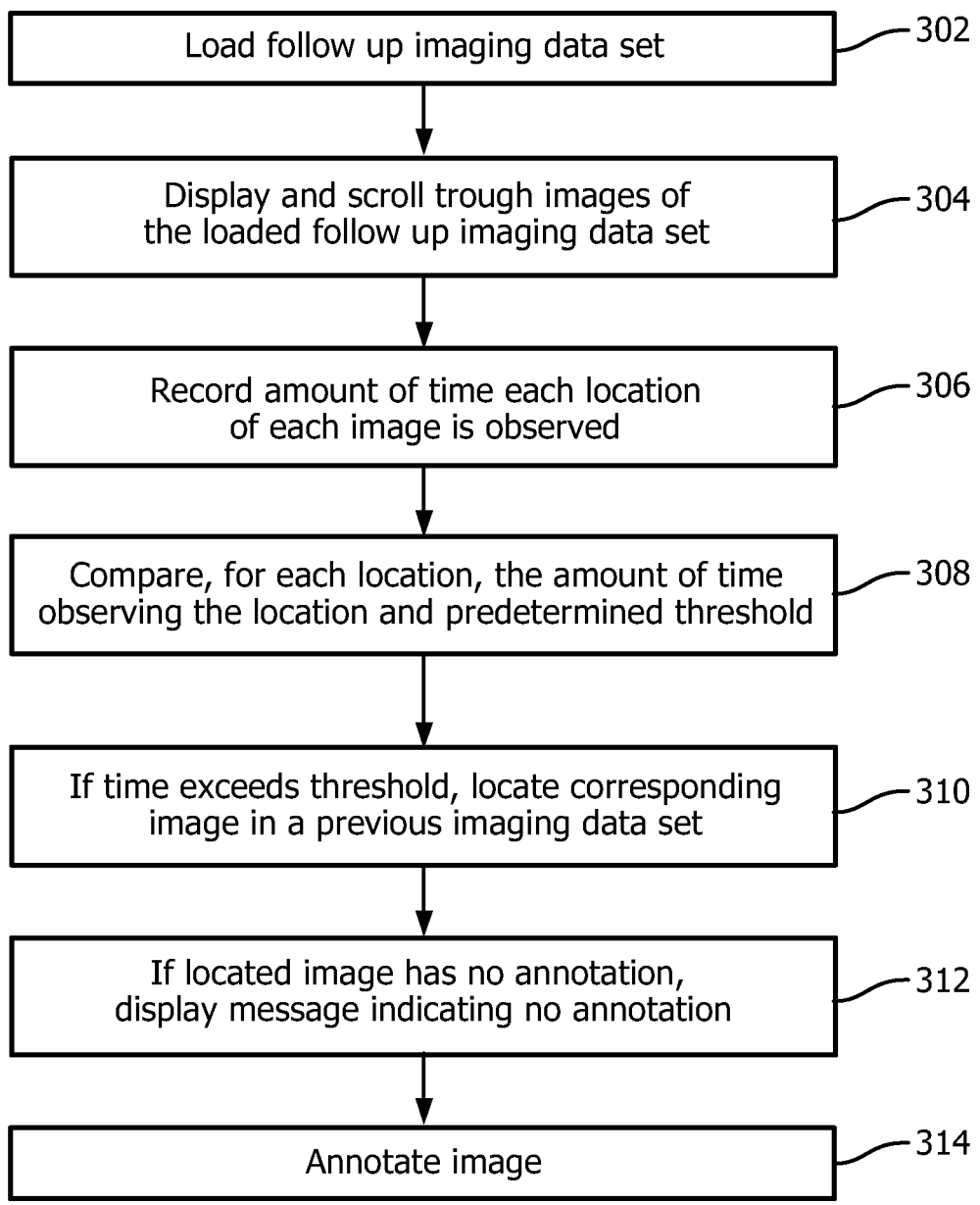
FIG. 3 illustrates a method for identifying and displaying a previous image without an annotation in a previously acquired data set corresponding to a current image with a finding of interest in a current data set.
Figure 4:
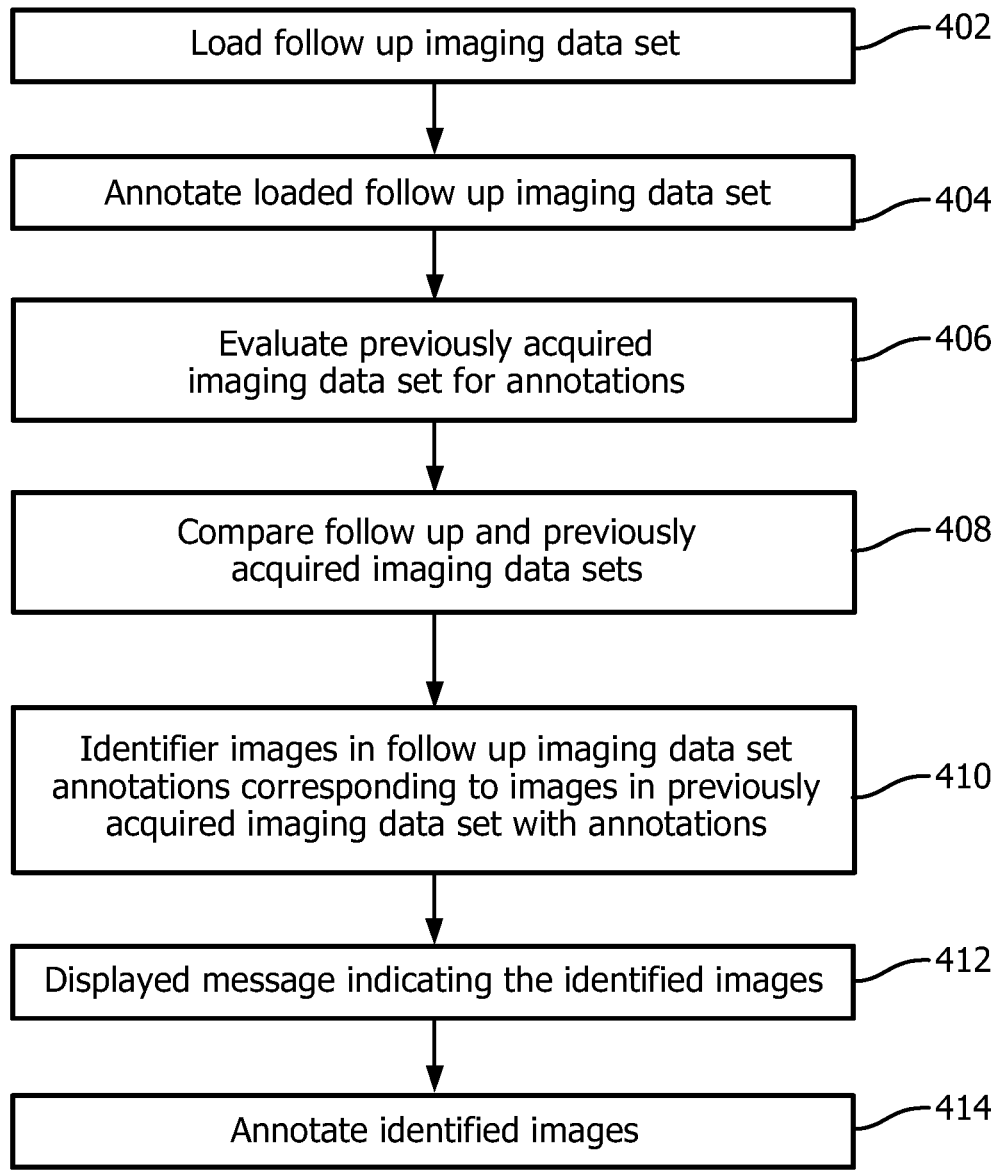
FIG. 4 illustrates a method for identifying and displaying an image in a current data set corresponding to a previous image with an annotation in a previously acquired data.

FIGS. 2, 3 and 4 illustrate example methods. For sake of brevity and explanatory purposes, FIGS. 2, 3 and 4 are disclosed in the context of how long an observer focuses on a region of an image. However, as disclose herein, the pattern at which the observer moves back and forth through a set of images can also be utilized.

It is to be appreciated that the ordering of the acts is not limiting. As such, other orderings are contemplated herein. In addition, one or more acts may be omitted and/or one or more additional acts may be included.

FIG. 2 illustrates a method for identifying and displaying a previous image with an annotation in a previously acquired data set corresponding to a current image with a finding of interest in a current data set.

At 202, a follow up imaging data set of a subject is loaded.

At 204, images of the loaded follow up imaging data set are displayed and scrolled through.

At 206, for each displayed image, an amount of time at which an observer observes each location, which covers particular tissue of the subject, of the displayed image is recorded.

At 208, for each location of each image, the amount of time spent observing each location is compared against a predetermined threshold time interval.

At 210, if the amount of time spent observing a particular location of an image exceeds the predetermined threshold time interval, then one or more imaging data sets from previous imaging examination of the subject is evaluated for a corresponding image with an annotation.

At 212, if the image with the annotation is located, indicia indicating the image is located is visually displayed.

At 214, if the located image is confirmed, then at least one of the located image or the annotation is concurrently displayed with the displayed image for comparison.

FIG. 3 illustrates a method for identifying and displaying a previous image without an annotation in a previously acquired data set corresponding to a current image with a finding of interest in a current data set.

At 302, a follow up imaging data set of a subject is loaded.

At 304, images of the loaded follow up imaging data set are displayed and scrolled through.

At 306, for each displayed image, an amount of time at which an observer observes each location, which covers particular tissue of the subject, of the displayed image is recorded.

At 308, for each location of each image, the amount of time spent observing each location is compared against a predetermined threshold time interval.

At 310, if the amount of time spent observing a particular location of an image exceeds the predetermined threshold time interval, then one or more imaging data sets from previous imaging examination of the subject is evaluated for a corresponding image with an annotation.

At 312, if a corresponding image without an annotation is located, a message indicating such an image has been located is displayed.

At 314, the image is annotated.

FIG. 4 illustrates a method for identifying and displaying an image in a current data set corresponding to a previous image with an annotation in a previously acquired data.

At 402, a follow up imaging data set of a subject is loaded.

At 404, images with findings of interest are annotated in the follow up imaging data set.

At 406, a previously acquired imaging data set is evaluated for annotations.

At 408, the previously acquired imaging data set and the follow up imaging data set are compared.

At 410, images in the follow up imaging data set that do not include annotations and that correspond to images in the previously acquired imaging data that do have annotations are identified.

At 412, a message indicating the identified images is displayed.

At 414, the identified images are annotated.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   detecting a focus of attention of an observer of a first anatomical image of a set of images;
   determining, in response to the detected focus of attention, that a location in the first anatomical image includes a tissue with a finding of interest;
   identifying a second anatomical image from an earlier acquired imaging data set comprising earlier acquired images, with a same portion of the tissue as the first anatomical image by determining that a distance between a first annotation of the first anatomical image and a second annotation of the second anatomical image is below a threshold; and
   visually displaying graphical indicia, concurrently with the first anatomical image, that identifies the second anatomical image.

2. The method of claim 1, the detecting of the focus of attention, comprising:
   determining the observer is dwelling on a particular region of the first anatomical image, wherein the location is the particular region.

3. The method of claim 1, the detecting of the focus of attention, comprising:
   determining an amount of time the observer spends observing the location of the first anatomical image;
   comparing the amount of time the observer spends observing the location of the first anatomical image with a predetermined threshold time interval; and
   determining the location of the first anatomical image includes the tissue with the finding of interest in response to determining that the amount of time the observer spends observing the location exceeds the predetermined threshold time interval.

4. The method of claim 3, further comprising:
   employing eye tracking to determine the amount of time the observer spends observing the location, in particular employing eye tracking to track at least one of a line of sight or a movement of an eye of the observer; and determining the amount of time the observer spends observing the location of the anatomical image based on at least one of the tracked line of sight or the tracked eye movement.

5. The method of claim 1, further comprising:

displaying the second anatomical image and/or an annotation of the second anatomical image in response to receiving an input indicating the graphical indicia has been actuated.

6. The method of claim 1, further comprising:

propagating the second annotation of the second anatomical image to the first anatomical image, and/or at least one of adding a third annotation to the first anatomical image or changing the second annotation of the second anatomical image.

7. The method of claim 1, wherein the second anatomical image is an initial image and the first anatomical image is a follow up image of the second anatomical image.

8. The method of claim 1, further comprising:

evaluating the earlier acquired images;

identifying annotations in the evaluated earlier acquired images;

determining a third anatomical image of the set of images, corresponds to a fourth image of the earlier acquired images, does not include an annotation, wherein the third image of the earlier acquired images include an annotation; and displaying a second message that indicates the fourth image of the set of images does not include an annotation.

9. A system, comprising:

a sensor that senses a focus of attention of an observer of a first anatomical image of a set of images;

a processor configured to:

map the sensed focus of attention to the first anatomical image based on a display geometry of the monitor, determine a metric based on the map, compare the metric with a predetermined metric, determine that a location in the first anatomical image includes tissue with a finding of interest in response to the metric satisfying the predetermined metric, identify a second anatomical image from an earlier acquired imaging data set with a same tissue as the first anatomical image by computing a normalized weighted score between the first anatomical image and a plurality of images of the previously generated imaging data set; and a display monitor that displays graphical indicia that identifies the second anatomical image.

10. The system of claim 9, wherein the set of images is registered with the earlier acquired imaging data set, and the second anatomical image is identified based on the registration, and/or wherein the set of images is segmented based on the focus of attention, and the second anatomical image is identified based on the segmentation, and/or wherein the set of images and the earlier acquired imaging data set correspond to two different imaging modalities, the set of images and the earlier acquired imaging data set are fused, and the second anatomical image from the earlier acquired imaging data set is identified based on the fused images.

11. A non-transitory computer readable storage medium encoded with computer readable instructions, which, when executed by a processor, causes the processor to:

detect a focus of attention of an observer of a first anatomical image of a set of images;

determine, in response to the detected focus of attention, that a location in the first anatomical image includes tissue with a finding of interest;

determine a pattern of scrolling back and forth between a plurality of anatomical images of the set of images; and identify an anatomical image from an earlier acquired imaging data set, with a same tissue as the first anatomical image based on the pattern; and visually displaying graphical indicia, concurrently with the first anatomical image, that identifies the second anatomical image.

* * * * *